United States Patent [19]

Hora et al.

[11] Patent Number: 5,078,997

[45] Date of Patent: Jan. 7, 1992

[54] PHARMACEUTICAL COMPOSITION FOR INTERLEUKIN-2 CONTAINING PHYSIOLOGICALLY COMPATIBLE STABILIZERS

[75] Inventors: Maninder S. Hora, Rodeo; Nandini Katre, El Cerrito, both of Calif.; Kenneth A. Laderman, Baltimore, Md.

[73] Assignee: Cetus Corporation, Emeryville, Calif.

[21] Appl. No.: 339,971

[22] Filed: Apr. 18, 1989

Related U.S. Application Data

[63] Continuation-in-part of Ser. No. 218,708, Jul. 13, 1988, abandoned.

[51] Int. Cl.$^5$ .............................................. A61K 37/06
[52] U.S. Cl. .................................. 424/85.2; 424/85.1; 514/970
[58] Field of Search ................................ 424/85.1, 85.2; 514/970

[56] References Cited

U.S. PATENT DOCUMENTS

| | | | |
|---|---|---|---|
| 4,362,719 | 12/1982 | Cavazza | 424/316 |
| 4,412,990 | 11/1983 | Lundblad et al. | 424/101 |
| 4,440,679 | 4/1984 | Fernandes et al. | 424/101 |
| 4,457,916 | 7/1984 | Hayashi et al. | 424/101 |
| 4,460,574 | 7/1985 | Yabrov | 424/88 |
| 4,470,968 | 9/1984 | Mitra et al. | 424/187 |
| 4,496,537 | 1/1985 | Kwan | 424/85.1 |
| 4,507,281 | 3/1985 | Asculai et al. | 424/85.1 |
| 4,534,971 | 8/1985 | Fisher | 514/21 |
| 4,604,377 | 8/1986 | Fernandes et al. | 514/2 |
| 4,623,717 | 11/1986 | Fernandes et al. | 424/101 |
| 4,645,830 | 2/1987 | Yasushi et al. | 530/351 |
| 4,645,830 | 2/1987 | Yasushi et al. | 530/351 |
| 4,647,454 | 3/1987 | Cymbalista | 424/85.1 |
| 4,659,570 | 4/1987 | Terano | 424/85.1 |
| 4,675,183 | 6/1987 | Kato et al. | 424/85.1 |
| 4,675,184 | 6/1987 | Hasegawa et al. | 435/811 |
| 4,680,175 | 7/1987 | Estis et al. | 424/85.1 |
| 4,931,544 | 6/1990 | Katre et al. | 424/85.1 |
| 4,933,433 | 6/1990 | Tamblyn | 424/85.1 |

FOREIGN PATENT DOCUMENTS

| | | |
|---|---|---|
| 0082481 | 6/1983 | European Pat. Off. . |
| 0092918 | 11/1983 | European Pat. Off. . |
| 0123291 | 10/1984 | European Pat. Off. . |
| 0133767 | 3/1985 | European Pat. Off. . |
| 0150067 | 7/1985 | European Pat. Off. . |
| 0154316 | 9/1985 | European Pat. Off. . |
| 0158487 | 10/1985 | European Pat. Off. . |
| 0163111 | 12/1985 | European Pat. Off. . |
| 166996 | 1/1986 | European Pat. Off. . |
| 0168008 | 1/1986 | European Pat. Off. . |
| 229016 | 7/1987 | European Pat. Off. . |
| 231132 | 8/1987 | European Pat. Off. . |
| 284249 | 9/1988 | European Pat. Off. . |
| 3325223 | 7/1983 | Fed. Rep. of Germany . |
| 57-163317 | 10/1982 | Japan . |
| 59-181223 | 10/1984 | Japan . |
| 59-181224 | 10/1984 | Japan . |
| 60-260523 | 12/1985 | Japan . |
| 61-137828 | 6/1986 | Japan . |
| 61-293926 | 12/1986 | Japan . |
| 62-223129 | 10/1987 | Japan . |

OTHER PUBLICATIONS

Journal Immunol. 739, 1987, pp. 905–912, Susskind et al.
Reynolds et al, Surgery, 104(2), 1988, pp. 142–151.
Talbott et al., Am. J. Clin. Nutr. 46(4) 1987, pp. 659–664.
Noda et al., 1985, Chem. Abst. vol. 102:154794.
J. J. Tagman, Handbook of Pharmaceutical Excipients, 225–227.
J. Sedmak et al., 1981, Methods in Enzymology, 78:591–595.
J. Wang et al., 1980, Journal of the Parenteral Drug Assoc., 34:452–462.
S. L. Marcus et al., 1987, Cancer Research, 47:4028–4212.
L. J. Walsh et al., 1985, The Journal of Investigative Dermatology, 85:501–506.
K. Yukioka et al., 1988, Archives of Biochemistry & Biophysics, 260:45–50.
Wang et al., 1988, J. Parenteral Science and Technology 42(S4):1–26.

Primary Examiner—Garnette D. Draper
Attorney, Agent, or Firm—Philip L. McGarrigle

[57] ABSTRACT

The present invention is a pharmaceutical composition for proteins which are not stably soluble. The preferred protein is IL-2 and the preferred composition includes amino acids, vitamins, polymers, fatty acids or low molecular weight acids.

14 Claims, 2 Drawing Sheets

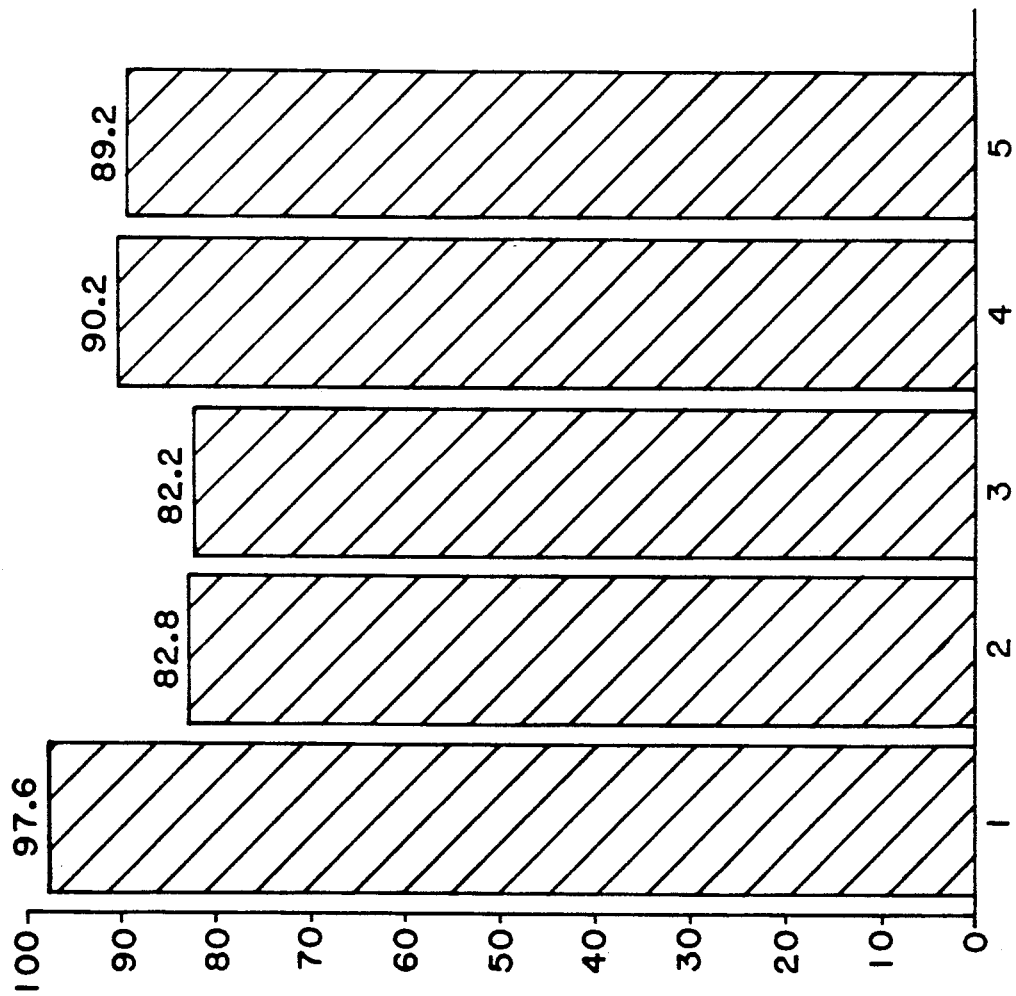

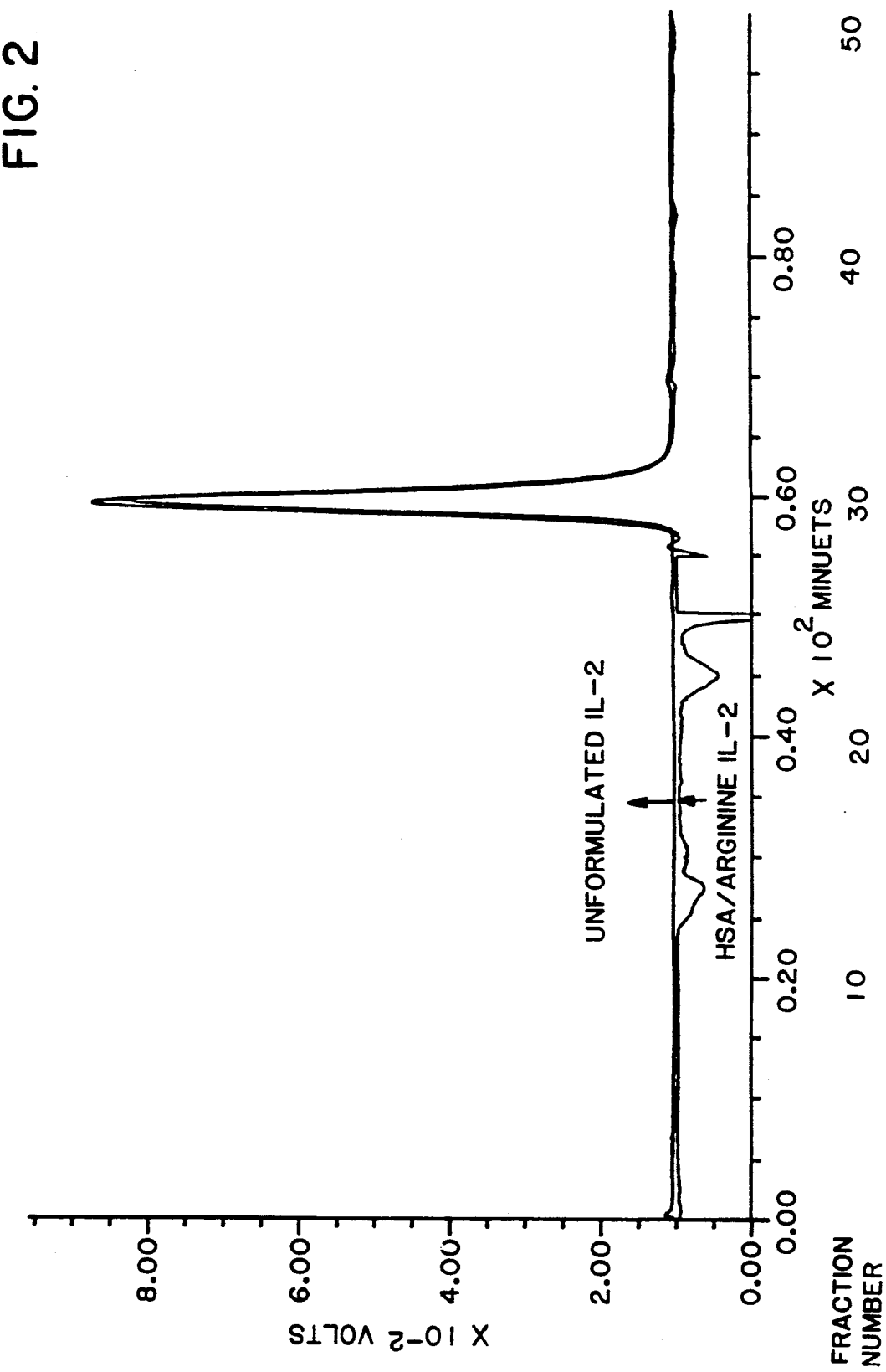

PHARMACEUTICAL COMPOSITION FOR INTERLEUKIN-2 CONTAINING PHYSIOLOGICALLY COMPATIBLE STABILIZERS

The present application is a continuation-in-part of copending U.S. Ser. No. 218,708, filed July 13, 1988, now abandoned which is hereby incorporated by reference in its entirety.

FIELD OF THE INVENTION

The present application relates to pharmaceutical compositions comprising interleukin-2 (IL-2) which are relatively difficult to maintain in solution. More specifically, the present invention relates to solubilizing and stabilizing IL-2 with amino acids, vitamins, fatty acids or salts of low molecular weight organic acids, and polymers, in a composition that may be administered to a subject.

BACKGROUND OF THE INVENTION

Interleukin-2 (IL-2) is a lymphokine which is produced by normal peripheral blood lymphocytes and is present in the body at low concentrations. It induces the proliferation of antigen or mitogen stimulated T cells after exposure to plant lectins, antigens, or other stimuli. IL-2 was first described by Morgan, D. A., et al., *Science* (1976) 193:1007–1008 and originally called T cell growth factor because of its ability to induce proliferation of stimulated T lymphocytes. It is a protein with a reported molecular weight in the range of 13,000 to 17,000 (S. Gillis and J. Watson, *J. Exp. Med.* (1980) 159:1709) and has an isoelectric point in the range of 6–8.5. It is now recognized that in addition to its growth factor properties it modulates various in vitro and in vivo functions of the immune system. IL-2 is one of several lymphocyte-produced messenger-regulatory molecules that mediate cellular interactions and functions.

IL-2 was initially made by cultivating human peripheral blood lymphocytes (PBL) or other IL-2-producing cell lines, see, for example, U.S. Pat. No. 4,401,756, and Mertelsmann, et al. European Patent Publication No. 92,163 and U.S. Ser. No. 603,580, filed Apr. 25, 1984. However, recombinant DNA technology has provided an alternative to PBLs and cell lines for producing IL-2. For example, Taniguchi, T., et al., *Nature* (1983) 302:305–310 and Devos, R., *Nucleic Acids Research* (1983) 11:4307–4323 have reported cloning the human IL-2 gene and expressing it in microorganisms. Various muteins of IL-2 have been reported. For example, see U.S. Pat. No. 4,518,584, to Mark, et al. and U.S. Pat. No. 4,752,585, to Koths, et al.

IL-2 produced in *E. coli* by recombinant DNA technology is not stably soluble in aqueous solutions at physiological pH (6–8). "Stably soluble" means that the IL-2 must be soluble for a prolonged time period in an aqueous medium. Because of this partial insolubility, various processes and additives have been devised to render IL-2 stably soluble. For example, IL-2 has been subjected to extreme pH changes (see European Patent Application 87100067.5) and has been combined with various surfactants or other additives (see U.S. Pat. No. 4,604,377). However, extreme pHs can be disadvantageous because they may induce severe structural unfolding and refolding which can create incorrect protein conformations or can denature the protein. Using certain additives, such as surfactants, can also be undesirable. Chaotropic agents, such as urea and guanidine work to solubilize IL-2, but must be used at very high concentrations which is also undesirable. Furthermore, when some aqueous formulations containing soluble IL-2 are lyophilized, they may not maintain the IL-2 in solution upon reconstitution. Consequently, there is a need for a pharmaceutical composition which can overcome the problems of the prior art. This composition should: maintain IL-2 in solution even after lyophilization and be free from surfactants or other chemicals which may alter the IL-2 conformational behavior. This need has been fulfilled by the invention that is described below.

SUMMARY OF THE INVENTION

The present invention is a pharmaceutical composition that is stable, sterile and soluble in an aqueous medium even after lyophilization and reconstitution. It comprises: IL-2; a stabilizer selected from the group consisting essentially of: a mixture of arginine and carnitine, carnitine, betaine, pyridoxine, salts of capric acid or succinic acid, polyvinylpyrrolidone, or mixtures thereof. Preferably, the stabilizer comprises a mixture of arginine and carnitine. The composition may also comprise serum albumin, a sugar or sugar alcohol, or a buffer in addition to the stabilizer. Another preferred composition is arginine in combination with serum albumin.

Among other factors, it has been discovered that IL-2 can be rendered stably soluble using the compounds listed above. It has also been surprisingly discovered that IL-2 may be lyophilized, and reconstituted without any loss in stable solubility or bioactivity when it is stabilized by arginine/carnitine, betaine, pyridoxine, carnitine and serum albumin, polyvinylpyrrolidone, sodium caprate, sodium succinate, arginine/serum albumin, or mixtures thereof. The present invention is also advantageous because the IL-2 is solubilized without subjecting it to extreme pH's or the use of surfactants such as sodium dodecyl sulfate.

The present invention more specifically comprises a pharmaceutical composition that is stable, sterile, and soluble in an aqueous medium even after lyophilization and reconstitution, comprising: IL-2; a stabilizer comprising between 0.2 and 3.0 w/v % arginine and between 0.2 and 3.0 w/v % carnitine; between 2 and 6 w/v % sucrose; 0.01 and 0.3M citrate, whereby the resulting solution has a pH between 6 and 7.5. It also specifically comprises between: 0.25 and 3.0 w/v % arginine; 2.0 and 6.0 w/v % mannitol; 0.25 and 5.0 serum albumin; 0.01 and 0.3M citrate; at a pH between 6.0 and 7.5 before the IL-2 is added to between 0.1 mg/ml and 2.5 mg/ml.

BRIEF DESCRIPTION OF THE DRAWINGS

FIG. 1 is a chart showing the relative aggregation of various IL-2 compositions.

FIG. 2 is a size exclusion chromatography (SEC) profile of an unformulated IL-2 composition and an HSA/arginine composition.

DETAILED DESCRIPTION OF THE INVENTION

IL-2 can be produced by a prokaryotic microorganism or an eukaryotic cell that has been transformed with a native or modified human IL-2 DNA sequence. It has hydrophobic and hydrophilic regions, and is unglycosylated when produced in *E. coli*. The IL-2 DNA useful in the present invention encodes a protein having: (a) an amino acid sequence that is essentially identical to the amino acid sequence of native human IL-2, including the disulfide bond to the cysteines at positions 58 and 105, and (b) has biological activity that is similar to native human IL-2. Substantial identity of amino acid sequences means the sequences are identical or differ by one or more amino acid alterations (deletions, additions, substitutions) that do not cause an adverse functional dissimilarity between the synthetic protein and native human interleukin-2. Examples of such proteins see: European Patent Application No. 83101035.0 filed Feb. 3, 1983 (published Oct. 19, 1983 under Publication No. 91539); European Patent Application No. 82307036.2 filed Dec. 22, 1982 (published Sept. 14, 1983 under No. 88195); the recombinant IL-2 muteins described in European Patent Application No. 83306221.9 filed Oct. 13, 1983 (published May 30, 1984 under No. 109748) which is the equivalent to Belgian Patent No. 893,016, commonly owned U.S. Pat. No. 4,518,584, and the recombinant IL-2 described in this application.

The precise chemical structure of IL-2 depends on a number of factors. As ionizable amino and carboxyl groups are present in the molecule, a particular protein may be obtained as a acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-transnational processing systems of the producing host; other such modifications may be introduced in vitro. In any event, such modifications are included in the definition of protein herein so long as the activity of the protein is not destroyed. It is expected that such modifications may quantitatively or qualitatively affect the activity, either by enhancing or diminishing the activity of the protein, in the various assays. Further, individual amino acid residues in the chain may be modified by oxidation, reduction, or other derivatization, and the protein may be cleaved to obtain fragments which retain activity. Such alterations which do not destroy activity do not remove the protein sequence from the definition of IL-2 herein.

Finally, modifications to the primary structure itself, by deletion, addition, or alteration of the amino acids incorporated into the sequence during translation, can be made without destroying the activity of the protein. For example, at least one cysteine residue which: is not essential to biological activity; is present in the biologically active protein; and is free to form a disulfide link, may be deleted or replaced with a conservative amino acid to eliminate sites for intermolecular crosslinking or incorrect intramolecular disulfide bond formation. Such modified proteins, known as "muteins", are described in U.S. Pat. Nos. 4,518,584 issued May 21, 1985 and 4,752,585 issued June 4, 1988. A conservative amino acid alteration in this context is defined as one which does not adversely affect biological activity and involves substitutions or deletion of the cysteine at position 125 or at position 104 (numbered in accordance with the native molecular). The preferred conservative amino acids that are useful to replace cysteine are: serine, alanine, threonine, glycine, valine, leucine, isoleucine, tyrosine, phenylalanine, histidine, and tryptophan. The preferred conservative amino acids that are useful to replace methionine are the same as for cysteine with the addition of asparginine and glutamine, but exclude histidine and tryptophan. A preferred IL-2 mutein has the cysteine at position 125 replaced with a serine residue and/or the methionine at amino acid position 104 replaced with an alanine residue. Other preferred IL-2 muteins include those which have as many as six N-terminal deletions. For example, des-ala1 des-pro2 des-thr3 des-ser4 des-ser5 des-ser6 IL-2 is an N-minus six mutein, other muteins may have fewer amino acid deletions. Specifically preferred muteins are des-ala1 des-pro2 des-thr3 des-ser4 ala104 ser125 IL-2, and des ala, ser125 IL-2, to name a few.

As mentioned previously, recombinant IL-2 can be produced by prokaryotic microorganism or eukaryotic cells. Preferably, the IL-2 is produced by transforming a prokaryotic microorganism with DNA to produce a protein that possesses native human IL-2 activity. Examples of transformed microorganisms are described in the European patent applications and U.S. patents noted above. Bacteria are preferred prokaryotic microorganisms for producing IL-2 and *E. coli* is especially preferred. A typical transformed microorganism useful in the present invention is *E. coli* K-12, strain MM294, transformed with plasmid pLW1 (deposited at the American Type Culture Collection on Aug. 4, 1983 by Cetus Corporation under the provisions of the Budapest Treaty and having accession No. 39,405). Synthetic recombinant IL-2 can also be made in eukaryotes, such as yeast or human cells.

Processes for growing, harvesting, disrupting, or extracting the IL-2 from cells are substantially described in U.S. Pat. Nos. 4,604,377; 4,738,927; 4,656,132; 4,569,790; 4,748,234; 4,530,787; 4,572,298; U.S. Ser. Nos. 167,144; 48,408 and (Cetus case 2197.2, filed May 31, 1988) which are hereby incorporated by reference in their entireties. Other procedures for purifying native IL-2 from T cells are described by Watson, J. et al., *J. Exp. Med.* (1979) 150:849-861; Gillis, S., et al., *J. Immunology* (1980) 124:1954-1962; Mochizuki, D. Y., et al., *J. Immun. Meth.* (1980) 39:185-201; Welte, K., et al., *J. Exp. Med.* (1982) 156:454-464; and European Patent Applications 83103582.9 (published Oct. 26, 1983 under No. 92163 and 83400938.3 published Nov. 16, 1983 under No. 94317) which are also incorporated by reference in their entireties.

After the IL-2 is produced and purified it may be incorporated into a pharmaceutical composition for application in human and veterinary therapeutics, such as cancer therapy and the treatment of infectious diseases. As composition, it is parenterally administered to the subject by methods known in the art. This composition may contain other compounds that increase the effectiveness or promote the desirable qualities of IL-2. The composition must be safe for administration via the route that is chosen, it must it must be sterile, retain bioactivity, and it must stably solubilize the IL-2. To maintain the sterility and to increase the stability of IL-2, the composition is lyophilized and reconstituted prior to use. As mentioned previously, many proteins may become insoluble after lyophilization. One benefit of the present invention is that the IL-2 remains soluble even after lyophilization and reconstitution.

In the present invention, various compounds are used as stabilizers for IL-2. "Stabilizer" is defined as an amino acid, vitamin, polymer, fatty acid, or a salt of a low molecular weight organic acid which will cause IL-2 to remain stably soluble in an aqueous solution. One important advantage of the present invention is that the present stabilizers will cause the IL-2 to remain in solution even after lyophilization and reconstitution. Another important advantage of the present invention is that some of these stabilizers exist in the body and many have a history of being injected into humans. Thus, they may be considered relatively safe because they do not present the same toxicity problems as do other formulants.

Preferred amino acids are the levo rotatory (L) forms of carnitine, arginine, and betaine, more preferred amino acid stabilizers are arginine, or a mixture of arginine and carnitine, the most preferred amino acid stabilizer is a mixture of carnitine and arginine. A preferred vitamin is pyridoxin ($B_6$), preferably as a hydrochloride salt, either alone or in combination with the amino acids. A preferred polymer is polyvinylpyrrolidone (PVP) with an average molecular weight between 2 and 3 thousand, more preferably about 2.5 thousand; or polyethylene glycol (PEG) with an average molecular weight between 3 and 5 thousand, more preferably about 4 thousand. Polymers outside of these ranges do not work as satisfactorily. A preferred fatty acid is capric acid and a preferred salt of a low molecular weight organic acid is succinic acid. More preferably these acids are sodium salts.

The pH of the combination is preferably adjusted to between 5.0 and 8.5 before adding the IL-2, more preferably between 6.0 and 8.0, most preferably between 6.0 and 7.5. When carnitine is used singly to stabilize IL-2, the solution pH will be approximately 3-3.5. Consequently, it is preferred to include an additional factor such as serum albumin. The serum albumin may be derived from humans, pigs, cows, and the like. Similarly, when arginine is used alone to stabilize IL-2 the solution pH may be between 9.5 and 10.5. A mixture of arginine and serum albumin (before IL-2 addition) within the pH range of 6 to 8.5 would give a pharmaceutically acceptable formulation. When both arginine and carnitine are used as the stabilizer, it is preferred to mix them together to bring the pH into a range between 5.0 and 8.5, more preferably between 6.0 and 8.0, most preferably between 6.0 and 7.5 before adding the IL-2. This combination is most preferred.

Typically, the stabilizer concentration is between 0.1 and 10 w/v %, more preferably between 0.25 and 4.5 w/v %. (Each component is expressed in terms of its weight versus the final liquid volume). When either arginine, carnitine, or betaine is used individually their concentrations are between 0.1 and 5.0 w/v %, more preferably between 0.2 and 3.0 w/v %. When arginine and carnitine are mixed together their individual concentrations are also in this range. The ratio between arginine and carnitine is preferably between 0.8 and 1.0, more preferably between 0.85 and 0.90. When serum albumin is used its concentration is between 0.25 and 5.0 w/v %, more preferably between 0.5 and 3.0 w/v %. The preferred vitamin, polymer, or fatty acid concentration is between 0 and 10 w/v %, more preferably between 1 and 5 w/v, most preferably between 1 and 3%. The preferred concentration of the salt of a low molecular weight organic acid is between 0 and 1M, more preferably between 0.05 and 0.5M, most preferably between 0.1 and 0.3M.

Without wishing to be bound by theory, it is believed that the stabilizers may interact with the hydrophobic and hydrophilic regions of IL-2 to protect it from aggregating or forming dimers. These loose complexes between the stabilizer and IL-2 are believed to keep the protein in solution even after reconstitution from the lyophilized state. It is also believed that the stabilizers of the present invention may remain bound to the protein during lyophilization to protect it from conformational changes, dimer formation, or aggregation.

In this invention it is also preferred to include sugars or sugar alcohols in the compositions. Sugar is defined as mono, di, or polysaccharides, or water-soluble glucans, including for example fructose, glucose, mannose, sorbose, xylose, maltose, lactose, sucrose, dextran, pullulan, dextrin, cyclodextrin, soluble starch, hydroxyethyl starch and carboxymethylcellulose-Na. Sucrose is the most preferred. Sugar alcohol is defined as a $C_4$-$C_8$ hydrocarbon having an —OH group and includes for example mannitol, sorbitol, inositol, galacititol, dulcitol, xylitol and arabitol; mannitol is the most preferred. The sugars or sugar alcohols mentioned above may be used individually or in combination. There is no fixed limit to the amount used, as long as the sugar or sugar alcohol is soluble in the aqueous preparation. Preferably, the sugar or sugar alcohol concentration is between 1.0 w/v % and 7.0 w/v %, more preferably between 2.0 and 6.0 w/v %.

It is also preferred to use a buffer in the composition to minimize pH changes in the solution before lyophilization or after reconstitution. Most any physiological buffer may be used, but citrate, phosphate, succinate, or glutarate buffers, or mixtures thereof are preferred. Most preferred is a citrate buffer. Preferably, the concentration is from 0.01 to 0.3M.

The present composition is preferably constructed by premixing the stabilizers and other formulants, such as sugar or sugar alcohol, water, and buffer. At this time the pH is preferably adjusted to between 5.0 and 8.5, more preferably to between 6.0 and 8.0, most preferably 6.0 and 7.5. Adjusting the pH prior to IL-2 addition can reduce the risk of denaturing IL-2. Preferred pH adjusters can be the stabilizers themselves or compounds that will not interfere with the functions of the formulants. After pH adjustment, the IL-2 is preferably added. Preferably the IL-2 is added to between 0.05 and 5.0 mg/ml, more preferably to between 0.1 and 2.0 mg/ml, most preferably between 0.5 mg/ml and 1.5 mg/ml. Appropriate mechanical devices are preferably provided for achieving a proper mix of constituents. The final composition pH is preferably in the same range as that shown above.

After the liquid pharmaceutical composition is prepared it is preferably lyophilized to prevent degradation and to preserve sterility. Methods for lyophilizing liquid compositions are known to those of ordinary skill in the art. Just prior to use, the composition may be reconstituted with a sterile diluent which may include additional ingredients. Upon reconstitution the composition is preferably administered to subjects using methods known to those skilled in the art.

The present pharmaceutical composition will now be illustrated by reference to the following examples which set forth particularly advantageous embodiments. However, it should be noted these embodiments are illustrative and are not to be construed as restricting the invention in any way.

EXAMPLE 1

Preparation of Various IL-2 Compositions

Stock solutions of the stabilizers, IL-2, and other formulants were made to compare the various compositions. IL-2 was produced and purified using a method similar to that disclosed in U.S. Ser. Nos. 167,144 now abandoned and 48,408 now abandoned which are hereby incorporated by reference in their entireties. The stock solutions contained the subject ingredients in 10 mM citrate buffer at pH 6.5 and include the following solutions: 2.3 mg/ml IL-2 (IL-2 A); 3.3 mg/ml IL-2 (IL-2 B); 20% L-carnitine; 8% L-arginine/9% L-carnitine chloride; 20% mannitol; 20% sucrose; 10% pyridoxine hydrochloride; 1% HSA/1% L-carnitine at pH 5.6; 5.0 HSA/0.2% L-arginine, pH 7.5; 20% L-betaine; 10% PVP 2.5 KD; 10% PEG 4KD; 10% sodium caprate; 0.5M sodium succinate; 10 mM citrate buffer at pH 6.5; and 100 mM citrate buffer at pH 6.5. Percents are in w/v %. If necessary, 10 mM citrate buffer was added to bring the total composition volume to 1 ml, however a 100 mM citrate buffer was added with HSA composition to bring it to 1 ml.

The following compositions were made with the appropriate amounts of the following compounds:

L Carnitine Chloride—1%, 5%, 10% solutions were made by combining 0.5 ml of IL-2 A with appropriate amounts of 20% carnitine chloride. A second 1% solution was made as above having 5% sucrose and 15% mannitol.

Pyridoxine Hydrochloride—2% and 4.5% solutions were made by combining 0.5 ml of IL-2 A with sucrose (final conc. of 2.5%), mannitol (final conc. of 7.5%), and pyridoxine hydrochloride.

Arginine and Carnitine—three different solutions were made. The solution first contained 0.5 ml of IL-2 A with 0.32 ml of 8% arg/9% carn; the second solution contained the first solution plus sucrose (final conc. of 5%); and the third solution contained the first solution plus sucrose (final conc. of 2.5%) and mannitol (final conc. of 15%).

HSA—one HSA solution was made in combination with carnitine to a final concentration of 0.5% HSA/0.5% carn. It included: 0.3 ml of Il-2 B; an appropriate amount of the 1% HSA/1% carnitine solution; and 100 mM citrate buffer. Another HSA solution was made in combination with arginine to a final concentration of 2.5% HSA/0.1% arginine. It included 0.3 ml of IL-2 B, an appropriate amount of 5% HSA/0.2% arginine solution in 100 mM citrate buffer.

Betaine—1%, and 10% solutions of betaine were made by combining 0.5 ml of IL-2 A with 20% betaine.

PVP—1%, 2%, and 5% solutions of PVP were made by combining 0.33 ml of IL-2 B with 10% PVP.

PEG—1%, 2%, and 5% solutions of PEG were made by combining 0.33 ml of IL-2 B with appropriate amounts of 10% PEG (4KD).

Sodium Caprate—1%, 2%, and 5% solutions of sodium caprate were made by combining 0.33 ml of IL-2 B with 10% sodium caprate.

Succinate—0.5M, 0.1M, and 0.125M solutions of sodium succinate were made by combining 0.33 ml of IL-2 B with 0.5M sodium succinate.

As mentioned above, the compositions were brought to 1 ml by 10 mM citrate buffer with the exception of the HSA compositions which had 100 mM citrate buffer.

EXAMPLE II

Lyophilization and Reconstitution

Each solution made in Example 1 was lyophilized and reconstituted to 1 ml using water for injection. Visual inspection and light scattering analysis showed that each solution was clear. This indicates that the IL-2 was stably soluble.

Various other compositions were made, lyophilized, and reconstituted then tested for clarity. Clarity was tested by a light scattering technique in which 1 ml was placed in a fluorimeter to measure the amount of 510 nm light scattered from a sample at 90 degrees. The results are shown in Table I. Each sample composition contained one mg/ml IL-2, the specific stabilizer(s), and possibly a bulking agent. The bulking agents are sucrose (S), and mannitol (M).

TABLE I

| Light Scattering Results Of Various Formulations | | | | |
|---|---|---|---|---|
| Stabilizer(s) | Bulking Agents | Immediately After Reconst. | Reconst. Soln. held @ RT for 24 hr | Reconst. After 4 wk @ 37° C. |
| 0.1% Arginine + 2.5% HSA | — | 115 | 292 | 206 |
| 0.125% Arginine + 0.5% HSA | 2% S | 246 | 260 | 250 |
| 0.125% Arginine + 0.5% HSA | 1.5% M + 0.5% S | 279 | 196 | 110 |
| 0.5% Carnitine + 0.5% HSA | 4% S | 339 | 239 | 83 |
| 0.5% Carnitine + 0.5% HSA | 3% M + 1% S | 246 | 147 | 140 |
| 0.25% Carnitine + 0.25% HSA | 4% S | 413 | 348 | 203 |
| 0.25% Carnitine + 0.25% HSA | 3% M + 1% S | 403 | 345 | 145 |
| 4% Arginine + 4.5% Carnitine | 5% S | — | 241 | 248 |
| 4% Arginine + 4.5% Carnitine | 3.5% M + 1.5% S | — | 214 | 375 |
| 2% Arginine + 2.25% Carnitine | 7% S | 204 | 174 | 169 |
| 2% Arginine + 2.25% Carnitine | 5% S | 229 | 196 | 190 |

TABLE I-continued

Light Scattering Results Of Various Formulations

| Stabilizer(s) | Bulking Agents | Immediately After Reconst. | Reconst. Soln.held @ RT for 24 hr | Reconst. After 4 wk @ 37° C. |
|---|---|---|---|---|
| 2% Arginine + 2.25% Carnitine | 3.5% M + 1.5% S | 685 | 335 | 473 |
| 1% Arginine + 1.125% Carnitine | 7% S | 236 | 334 | 271 |
| 1% Arginine + 1.125% Carnitine | 3.5% M | 291 | 172 | 271 |
| 0.5% Arginine + 0.56% Carnitine | 7% S | 339 | 328 | 287 |
| 0.5% Arginine + 0.56% Carnitine | 5% S | 274 | 408 | 371 |
| 0.5% Arginine + 0.56% Carnitine | 3.5% M + 1.5% S | 290 | 264 | 361 |
| 0.25% Arginine + 0.28% Carnitine | 7% S | 450 | 433 | 330 |
| 0.25% Arginine + 0.28% Carnitine | 5% S | 368 | 471 | 465 |
| 0.25% Arginine + 0.28 Carnitine | 3.5% M + 1.5% S | 427 | 483 | 357 |
| 0.125% Arginine + 0.14% Carnitine | 7% S | 500 | 560 | 408 |
| 0.125% Arginine + 0.14% Carnitine | 5% S | 493 | 515 | 568 |
| 0.125% Arginine + 0.14% Carnitine | 3.5% M + 1.5% S | 541 | 376 | 880 |
| 2% Betaine | 3.5% M + 1.5% S | 260 | 55 | 266 |
| 1% Betaine | 5% S | 590 | 582 | 534 |

S = Sucrose
M = Mannitol
RT = Room Temperature

EXAMPLE III

The Effect of Time and Temperature on the Composition

Two IL-2 compositions were made and named ACS-001 and ACS-002. They both contained 2% arginine, 2.25% carnitine chloride, 5% sucrose, 1 mg/ml IL-2, in a pH 6.5 citrate buffer. 1 ml volumes of these solutions were lyophilized and stored under the conditions and for the times listed in Table II. The light scattering values were measured as in Example II.

TABLE II

Stability Under Various Times and Temperatures

| Conditions of storage | | Light Scattering Value for Composition | |
|---|---|---|---|
| Temperature | Time on shelf | ACS-001 | ACS-002 |
|  | INITIAL | 255 | 151 |
| −20° C. | 7 weeks | 172 | 123 |
|  | 11 weeks |  | 159 |
|  | 12 weeks | 150 |  |
|  | 16 weeks | 203 |  |
| 4° C. | 2 weeks |  | 358 |
|  | 3 weeks |  | 246 |
|  | INITIAL | 255 | 151 |
|  | 6 weeks | 397 |  |
|  | 7 weeks | 187 | 163 |
|  | 11 weeks |  | 223 |
|  | 12 weeks | 191 |  |
|  | 16 weeks | 252 |  |
| 37° C. | 5 weeks | 761 |  |
|  | 7 weeks | 729 | 551 |
|  | 11 weeks |  | 432 |
|  | 12 weeks | 334 |  |
|  | 16 weeks | 255 |  |

Note: A light scattering value of less than 1000 usually represents a clear solution.
Conclusion: The compositions yield clear solutions after storage even at 37° C. up to 16 weeks.

Additionally, a formulation was prepared which contained 2.5% HSA, 0.25% L-arginine, 2% mannitol, 1 mg/ml IL-2 in 30 mM Citrate buffer (final pH 7.4). Lyophilized compositions were stored under the various conditions shown below.

TABLE III

| Temperature | Time of Shelf | Light Scattering Value |
|---|---|---|
|  | INITIAL | 5 |
| 37° C. | 3 weeks | 22 |
|  | 6 weeks | 36 |
| 4° C. | 3 weeks | 47 |
|  | 6 weeks | 26 |

EXAMPLE IV

IL-2 Aggregate Formation

An ultracentrifuge experiment was designed to detect IL-2 aggregate formation. ACS-001 and ACS-002 were lyophilized and stored at 4° before reconstitution. These compositions were measured against an unformulated solution of IL-2 which contained 1 mg/ml IL-2 in citrate buffer. The solutions that were tested were: an unformulated IL-2 solution; an ACS-001 composition stored for six weeks; an ACS-002 composition stored for one week; an ACS-001 composition stored for eight weeks; and an ACS-002 composition stored for three weeks. They were placed in an ultracentrifuge and spun at 100,000 rpm for 60 minutes. Analysis of the supernatant showed that the unformulated IL-2 (freshly prepared) had 97.6% of the IL-2 in an non-aggregated form. The ACS-001 sample stored for six weeks was 82.8% non-aggregated, the ACS-002 sample stored for one week was 82.2% non-aggregated, the ACS-001 sample stored for eight weeks was 90.2% non-aggregated and the ACS-002 sample stored for three weeks was 89.2% non-aggregated. This shows that the present compositions are substantially non-aggregated during storage for at least eight weeks. See FIG. 1.

Two experiments were performed to detect IL-2 aggregate formation in pharmaceutical compositions. They were: the Western blot and sodium dodecyl sulfate-polyacrylamide gel electrophoresis (SDS-PAGE) analyses.

The Western blot tests were conducted by taking the reconstituted samples shown in Table I and running them on a polyacrylamide gel. The gel samples were then transferred to a nitrocellulose filter and the IL-2 was located by staining with a monoclonal antibody to IL-2. No significant dimer formation was evident for the present formulations.

The SDS-PAGE analysis was conducted on similar samples. No dimer formation was evident by this procedure.

EXAMPLE V

Residual Moisture

The two lyophilized formulations noted above, ACS-001 and ACS-002, were tested for residual moisture because it may be detrimental to protein stability upon storage. The percent moisture in these compositions was determined by using a Karl Fischer coulometer. The results are shown in Table III.

TABLE III

| Residual Moisture | | | |
|---|---|---|---|
| Conditions of Storage | | % Moisture in Composition | |
| Temperature | Time | ACS-001 | ACS-002 |
| | INITIAL | 0.30 | 0.20 |
| $-20°$ C. | 8 weeks | | 0.20 |
| | 12 weeks | 0.27 | |
| $4°$ C. | 8 weeks | | 0.20 |
| $37°$ C. | 8 weeks | | 0.28 |
| | 12 weeks | | 0.20 |

These results indicate that the moisture content of the composition does not significantly increase under the accelerated storage conditions of 12 weeks at 37° C.

EXAMPLE VI

Bioactivity of IL-2 Compositions

Various IL-2 compositions were constructed and tested for bioactivity. The lyophilized compositions were stored for four weeks at 37° C. before being tested. The test used for bioactivity was a cell proliferation assay. For examples of typical assays see Gillis, S., et al., *J. Immunology*, 120:2027–2032 (1978); and Watson, J., *J. Exp. Med.*, 150:1510–1519 (1979). The results shown below indicate that the compositions retain substantial IL-2 bioactivity even after storage.

TABLE IV

| Bioactivity Of IL-2 Formulations | | |
|---|---|---|
| Excipient Composition | Storage Conditions | Specific Activity $\mu$/mg |
| 10 mM Citrate | — | $1.67 \times 10^7$ |
| 4% Arginine, 4.5 Carnitine Cl 5% Sucrose, 50 mM Citrate | 4 wks @ 37° C. | $4.96 \times 10^6$ |
| 2% Arginine, 2.25 Carnitine Cl 5% Sucrose, 50 mM Citrate | " | $4.99 \times 10^6$ |
| 1% Arginine, 1.12% Carnitine Cl 7% Sucrose, 50 mM Citrate | " | $7.30 \times 10^6$ |
| 1% Arginine, 1.12% Carnitine Cl 5% Sucrose, 50 mM Citrate | " | $4.55 \times 10^6$ |
| 2% Betaine, 3.5% Mannitol | " | $5.86 \times 10^6$ |
| 0.5% HSA, 0.125% Arginine | " | $8.0 \times 10^6$ |
| 0.25% HSA, 0.25% Carnitine Cl | " | $8.6 \times 10^6$ |

EXAMPLE VII

Protein Integrity

IL-2 integrity was checked using three procedures: reverse phase high pressure liquid chromatography (RP-HPLC); iso-electric focusing (IEF); and size exclusion chromatography (SEC).

RP-HPLC analysis employed an acetonitrile/trifloroacetic acid gradient on a Vydac C4 column to resolve protein peaks. Sizing HPLC used the Superose 12 gel filtration column at 0.5 ml/min with 0.1M ammonium sulphate/0.010M phosphate, pH 7.0 buffer. A liquid composition similar to ACS-001 and ACS-002 was analyzed immediately after reconstitution and after storage at 37° C. for 28 days. There was no change in the HPLC protein profile.

IEF analysis compared compositions similar to those analyzed by RP-HPLC analysis. IEF gels were run on Phase 3-9 precast gels, and stained. No differences were observed between samples.

SEC analysis was used for the compositions listed in Table I. It was performed by chromatography on a Superose-12 column. The results showed that the arginine/carnitine and the carnitine/HSA, arginine/HSA, compositions appear as stable as the starting compositions, whereas the betaine composition formed some dimers.

Additionally, FIG. 2 shows an SEC profile of an IL-2 which contained: 1 mg/ml IL-2; 2.5% HSA; 0.25% Arginine; 2% Mannitol; in 30 mM citrate buffer; at pH 7.4. The formulation was lyophilized and stored at 37° C. for 3 months, reconstituted and assayed by SEC. This profile shows that the IL-2 is present as a monomer even after 3 months at 37° C.

EXAMPLE VIII

Various compositions were formulated, stored, reconstituted, and assayed after extended storage. The details are given in Table V.

TABLE V

| Long-Term Stability of IL-2 Formulations All formulations contained 1 mg/ml of IL-2. | | | | | | |
|---|---|---|---|---|---|---|
| Sample | Formulation | Time on Shelf | Temp °C. | Light Scattering | Bioactivity $\mu$/mg | % Oligomers* |
| $D_1$ | 0.5% NaCaprate, 2% Sucrose, in 10 mM Citrate pH 7.0 | 14 months | 4° C. | 170 | $2.59 \times 10^7$ | 0.48 |
| $D_5$ | 0.1 M NaSuccinate, 5% Mannitol in 25 mM Citrate, pH 6.5 | 14 months | 4° C. | 185 | $4.57 \times 10^7$ | 0.17 |
| $F_1$ | 2% PEG-4000, 2% Sucrose in 10 mM Citrate, pH 6.5 | 13¼ months | 37° C. | 88 | $3.02 \times 10^7$ | 0.91 |
| $F_2$ | 2% PVP, 2% Sucrose in 10 mM Citrate, pH 6.5 | 13¼ months | 37° C. | 755 | $3.29 \times 10^7$ | 0.44 |

TABLE V-continued

Long-Term Stability of IL-2 Formulations
All formulations contained 1 mg/ml of IL-2.

| Sample | Formulation | Time on Shelf | Temp °C. | Light Scattering | Bioactivity μ/mg | % Oligomers* |
|---|---|---|---|---|---|---|
| ACS-001 | 2% Arginine, 2.25% Carnitine Cl, 5% Sucrose, 10 mM Citrate pH 6.5 | 14 months | 4° C. | 524 | $3.88 \times 10^7$ | 0.00 |
| | | | 37° C. | 121 | $2.69 \times 10^7$ | 0.00 |
| ACS-002 | Same as ACS-001 | 13 months | 4° C. | 274 | $2.98 \times 10^7$ | 0.00 |
| | | | 37° C. | 173 | $2.84 \times 10^7$ | 0.00 |
| ACS-003 | Same as ACS-001 | 10¼ months | 4° C. | 47 | $1.97 \times 10^7$ | 0.00 |
| | | | 37° C. | 249 | $2.28 \times 10^7$ | 0.00 |
| IL-2 | in 10 mM Citrate, pH 6-5 | Freshly purified | — | — | $0.9–4.0 \times 10^7$ | 0.00 |

*% Oligomers estimated by the reducing SDS-PAGE technique.

Conclusions from Table V:

(1) Formulations using sodium caprate, sodium succinate, PEG-4000 and PVP are very stable in terms of the clarity of solution and bioactivity. Less than 1% of oligomers are formed in 13–14 months.

(2) Arginine-carnitine formulated IL-2 is especially stable. The lyophilized plugs stored at even 37° C. for 10–14 months yield clear solutions upon reconstitution, retain full biological activity and form no detectable oligomers on SDS-PAGE.

The present invention has been described with reference to specific embodiments. However, this application is intended to cover those changes and substitutions which may be made by those skilled in the art without departing from the spirit and scope of the appended claims.

What is claimed is:

1. A pharmaceutical composition that is stable, sterile, and soluble in an aqueous medium, which can be lyophilized and reconstituted without losing its solubility, comprising IL-2 and a stabilizer, wherein the stabilizer is selected from the group consisting of: an arginine/carnitine mixture; carnitine; betaine; pyridoxine polyvinylpyrrolidone; salts of capric acid; or mixtures thereof.

2. A pharmaceutical composition in accordance with claim 1, wherein the stabilizer is selected from the group consisting of: an arginine/carnitine mixture; carnitine; or betaine.

3. A pharmaceutical composition in accordance with claim 1, wherein the stabilizer an is arginine/carnitine mixture.

4. A pharmaceutical composition in accordance with claim 1, wherein the stabilizer comprises betaine.

5. A pharmaceutical composition in accordance with claim 1, wherein the stabilizer comprises carnitine and the composition further comprises serum albumin.

6. A pharmaceutical composition in accordance with claim 1, wherein the concentration of IL-2 is between 0.1 and 2.0 mg/ml IL-2.

7. A pharmaceutical composition in accordance with claim 1, further comprising a sugar or sugar alcohol and a buffer.

8. A pharmaceutical composition in accordance with claim 7, wherein the sugar is sucrose and the buffer is citrate.

9. A pharmaceutical composition in accordance with claim 8, wherein the IL-2 is added to the composition after the sucrose, citrate, and stabilizer have been added and the pH adjusted to between 5 and 8.5.

10. A pharmaceutical composition that is stable, sterile and soluble in an aqueous medium even after lyophilization and reconstitution, comprising: IL-2; a stabilizer comprising between 0.2 and 3.0 w/v % arginine and between 0.2 and 3.0 w/v % carnitine; between 2 and 6 w/v % sucrose; 0.01 and 0.3M citrate, so that the resulting composition has a pH between 6 and 7.5.

11. A pharmaceutical composition in accordance with claim 10, wherein the concentration of IL-2 is between 0.1 and 2.0 mg/ml IL-2.

12. A pharmaceutical composition in accordance with claim 10, wherein the composition is in the lyophilized form.

13. A pharmaceutical composition in accordance with claim 10, wherein the composition is in liquid form.

14. A process for making a pharmaceutical IL-2 composition, comprising, admixing at least one of the stabilizers claimed in claim 1, a buffer, and a sugar or a sugar alcohol; ensuring that the pH of the solution containing the stabilizer, buffer, and sugar or sugar alcohol is between 6 and 8; and then adding IL-2 to the admixture.

* * * * *

UNITED STATES PATENT AND TRADEMARK OFFICE
CERTIFICATE OF CORRECTION

PATENT NO. : 5,078,997

DATED : January 7, 1992

INVENTOR(S) : Maninder S. Hora, et al

It is certified that error appears in the above-identified patent and that said Letters Patent is hereby corrected as shown below:

In column 12, line 62 and column 14, line 5, in Table V, change "u/mg" to --IU/mg--.

Signed and Sealed this

Fourth Day of May, 1993

Attest:

MICHAEL K. KIRK

Attesting Officer

Acting Commissioner of Patents and Trademarks